(12) United States Patent
Durschang et al.

(10) Patent No.: US 10,219,879 B2
(45) Date of Patent: *Mar. 5, 2019

(54) LITHIUM DISILICATE GLASS-CERAMIC, METHOD FOR PRODUCTION THEREOF AND USE THEREOF

(71) Applicants: FRAUNHOFER-GESELLSCHAFT zur Förderung der angewandten Forschung e.V., Munich (DE); VITA Zahnfabrik H. Rauter GmbH & Co. KG, Bad Säckingen (DE); DeguDent GmbH, Hanau (DE)

(72) Inventors: Bernhard Durschang, Rottendorf (DE); Jörn Probst, Kümach (DE); Norbert Thiel, Bad Säckingen (DE); Joachim Bibus, Bad Säckingen (DE); Markus Vollmann, Gelnhausen (DE); Udo Schusser, Alzenau (DE)

(73) Assignees: DEGUDENT GMBH, Hanau (DE); FRAUNHOFER-GESELLSCHAFT ZUR FORDERUNG DER ANGEWANDTEN FORSCHUNG E.V., Munich (DE); VITA ZAHNFABRIK H. RAUTER GMBH & CO. KG, Bad Sackingen (DE)

( * ) Notice: Subject to any disclaimer, the term of this patent is extended or adjusted under 35 U.S.C. 154(b) by 1439 days.

This patent is subject to a terminal disclaimer.

(21) Appl. No.: 14/274,235

(22) Filed: May 9, 2014

(65) Prior Publication Data

US 2014/0249016 A1  Sep. 4, 2014

Related U.S. Application Data

(63) Continuation of application No. 13/518,765, filed as application No. PCT/EP2010/007918 on Dec. 23, 2010, now Pat. No. 8,956,987.

(30) Foreign Application Priority Data

Dec. 23, 2009  (DE) ......... 10 2009 060 274

(51) Int. Cl.

| | |
|---|---|
| C03C 10/04 | (2006.01) |
| A61C 13/083 | (2006.01) |
| A61C 13/00 | (2006.01) |
| A61K 6/02 | (2006.01) |
| A61K 6/027 | (2006.01) |
| C03B 32/02 | (2006.01) |
| C03C 10/00 | (2006.01) |
| A61C 13/01 | (2006.01) |
| A61C 5/35 | (2017.01) |
| A61C 5/70 | (2017.01) |
| A61C 5/77 | (2017.01) |
| C03C 3/097 | (2006.01) |
| C03C 4/00 | (2006.01) |

(52) U.S. Cl.
CPC ............ *A61C 13/0006* (2013.01); *A61C 5/35* (2017.02); *A61C 5/70* (2017.02); *A61C 5/77* (2017.02); *A61C 13/01* (2013.01); *A61C 13/083* (2013.01); *A61K 6/024* (2013.01); *A61K 6/0245* (2013.01); *A61K 6/0273* (2013.01); *C03B 32/02* (2013.01); *C03C 3/097* (2013.01); *C03C 4/0021* (2013.01); *C03C 10/0027* (2013.01)

(58) Field of Classification Search
CPC ..... C03C 10/00; C03C 10/0009; A61K 6/024; A61K 6/0273
USPC ................................. 501/5; 106/35
See application file for complete search history.

(56) References Cited

U.S. PATENT DOCUMENTS

| | | | |
|---|---|---|---|
| 2,684,911 A | 7/1954 | Stookey | |
| 3,238,085 A | 3/1966 | Hayami et al. | |
| 4,515,634 A | 5/1985 | Wu et al. | |
| 5,507,981 A | 4/1996 | Petticrew | |
| 5,698,482 A | 12/1997 | Frank et al. | |
| 5,925,180 A | 7/1999 | Frank et al. | |
| 6,048,589 A * | 4/2000 | Suzuki et al. | 427/554 |
| 6,086,977 A * | 7/2000 | Suzuki et al. | 428/141 |
| 6,420,288 B2 * | 7/2002 | Schweiger et al. | 501/7 |
| 6,593,257 B1 * | 7/2003 | Nagata et al. | 501/4 |
| 7,166,548 B2 | 1/2007 | Apel et al. | |

(Continued)

FOREIGN PATENT DOCUMENTS

| | | |
|---|---|---|
| CA | 2213390 A1 | 3/1998 |
| CA | 2252660 A1 | 5/1999 |

(Continued)

OTHER PUBLICATIONS

Von Clausbruch et al., "Crystallization, Microstructure and Properties of Selected Glasses and Glass-Ceramics in the SiO2—Li2O—ZnO—K2O—P2O5 System," DGG Journal, vol. 1, No. 1, pp. 41-49 (2002).

(Continued)

Primary Examiner — Karl E Group
(74) Attorney, Agent, or Firm — Rothwell, Figg, Ernst & Manbeck, p.c.

(57) ABSTRACT

The invention relates to glass-ceramics based on the lithium silicate system which can be mechanically machined easily in an intermediate step of crystallization and, after complete crystallization, represent a very strong, highly-translucent and chemically-stable glass-ceramic. Likewise, the invention relates to a method for the production of these glass-ceramics. The glass-ceramics according to the invention are used as dental material.

3 Claims, No Drawings

(56) References Cited

U.S. PATENT DOCUMENTS

| | | | |
|---|---|---|---|
| 8,536,078 B2 * | 9/2013 | Ritzberger et al. | 501/6 |
| 8,557,150 B2 * | 10/2013 | Ritzberger et al. | 264/16 |
| 2002/0010063 A1 | 1/2002 | Schweiger et al. | |
| 2005/0209082 A1 | 9/2005 | Apel et al. | |
| 2007/0042889 A1 | 2/2007 | Apel et al. | |
| 2010/0083706 A1 | 4/2010 | Castillo | |
| 2011/0030423 A1 | 2/2011 | Johannes et al. | |
| 2011/0256409 A1 * | 10/2011 | Ritzberger et al. | 428/432 |
| 2012/0248642 A1 * | 10/2012 | Ritzberger et al. | 264/19 |
| 2013/0295523 A1 | 11/2013 | Durschang et al. | |

FOREIGN PATENT DOCUMENTS

| | | | |
|---|---|---|---|
| DE | 1421886 | A1 | 6/1969 |
| DE | 2451121 | A1 | 5/1975 |
| DE | 102004013455 | B3 | 9/2005 |
| DE | 102005028637 | A1 | 12/2006 |
| DE | 102007011337 | A1 | 9/2008 |
| EP | 0536572 | A1 | 4/1993 |
| EP | 0536479 | B1 | 9/1995 |
| EP | 069031 | A1 | 1/1996 |
| EP | 0827941 | A1 | 3/1998 |
| EP | 0916625 | A1 | 5/1999 |
| EP | 1505041 | A1 | 2/2005 |
| FR | 2655264 | A | 6/1991 |
| JP | 2011225441 | * | 11/2011 |
| SU | 908355 | A1 | 2/1982 |
| WO | 9532678 | A2 | 12/1995 |
| WO | 2012059143 | A1 | 5/2012 |

OTHER PUBLICATIONS

Borom et al., "Strength and Microstructure in Lithium Disilicate Glass-Ceramics", Journal of the American Ceramic Society, vol. 58, No. 9-10, pp. 385-391 (1975).

De Oliveira et al., "Sintering and Crystallization of a Glass Powder in the $Li_2O$—$ZrO_2$—$SiO_2$ System," Communications of the American Ceramic Society, vol. 81, No. 3, pp. 777-780 (1998).

Montedo et al. "Low Thermal Expansion Sintered LZSA Glass-Ceramics," American Ceramic Society Bulletin, vol. 87. No. 7, pp. 34-40 (2008).

Stookey, "Chemical Machining of Photosensitive Glass", Industrial and Engineering Chemistry, 45, pp. 115-118 (1993).

European Patent Office, International Search Report in International Application No. PCT/EP2010/007918 (dated Mar. 29, 2011).

European Patent Office, International Preliminary Report on Patentability in International Application No. PCT/EP2010/007918 (dated Mar. 29, 2011).

* cited by examiner

LITHIUM DISILICATE GLASS-CERAMIC, METHOD FOR PRODUCTION THEREOF AND USE THEREOF

This application claims priority to and is a continuation of U.S. application Ser. No. 13/518,765 filed Aug. 15, 2012, now U.S. Pat. No. 8,956,987, which is the national stage entry of PCT/EP10/07918 filed Dec. 23, 2010, which claims priority to DE 10 2009 060 274.7 filed Dec. 23, 2009, all of which are hereby incorporated by reference in their entirety.

The invention relates to glass-ceramics based on the lithium disilicate system which can be mechanically machined easily in an intermediate step of crystallisation and, after complete crystallisation, represent a very strong, highly-translucent and chemically-stable glass-ceramic. Likewise, the invention relates to a method for the production of these glass-ceramics. The glass-ceramics according to the invention are used as dental material.

Lithium disilicate glass-ceramics are well known from the literature and several patents are based on this glass-ceramic system. Thus, for example, self-glazed lithium disilicate glass-ceramic objects for the production of tableware are described in EP-B-536 479, in EP-B-536 572 lithium disilicate glass-ceramics which can be used, by scattering fine-particle coloured glass on the surface thereof, as lining elements for building purposes.

The main focus of patented lithium disilicate glass-ceramics is on dental applications. This is due to the fact that the crystallisation of lithium disilicate crystals is effected via a phase of lesser strength (lithium metasilicate) and the material system is consequently amenable inter alia to chair-side methods (see S. D. Stookey: "Chemical Machining of Photosensitive Glass", Ind. Eng. Chem., 45, pp. 115-118 (1993) and S. D. Stookey: "Photosensitively Opacifiable Glass" U.S. Pat. No. 2,684,911 (1954)). Investigations by Borom, e.g. M.-P Borom, A. M. Turkalo, R. H. Doremus: "Strength and Microstructure in Lithium Disilicate Glass-Ceramics", J. Am. Ceream Soc., 58, No. 9-10, pp. 385-391 (1975) and M.-P. Borom, A. M. Turkalo, R. H. Doremus: "Verfahren zum Herstellen von Glaskeramiken" (Method for the production of glass-ceramics), DE-A-24 51 121 (1974) show that glass-ceramics which comprise lithium metasilicate as main phase have reduced strength in comparison with glass-ceramics which comprise lithium disilicate as single crystalline phase.

This principle was used in order firstly to produce a glass-ceramic, in a two-step crystallisation process, which can be machined well mechanically, e.g. by means of CAD/CAM methods, and to process this subsequently in a second crystallisation step to form dental glass-ceramic. This method is suitable for being able to use dental restorations according to the so-called chair-side method. In the case of this method, an individually adapted crown/onlay/inlay is milled out of a glass-ceramic block after the first crystallisation step by means of CAD/CAM in the dentist's surgery, this is subjected to the second crystallisation step in a special oven and used directly in the first and only dental appointment for the patient (DE 10 2005 028 637).

In addition, in WO-A-95/32678 and U.S. Pat. No. 5,507,981, lithium disilicate glass-ceramics were described, which can be processed to form shaped dental products by means of hot-pressing by using a special compressible crucible. Furthermore, there are known, from DE-C-14 21 886, glass-ceramics based on $SiO_2$ and $Li_2O$ which contain large quantities of physiologically very questionable arsenic oxide. Also in U.S. Pat. No. 4,515,634 and in FR-A-2 655 264, lithium disilicate glass-ceramics which are suitable for the production of dental crowns and bridges are disclosed.

All known lithium disilicate glass-ceramics display inadequacies in the processing thereof to shaped products and/or in mechanical or visual properties and/or in chemical stability. In particular when used in the dental field, equally high requirements for all the mentioned properties must be fulfilled.

Starting herefrom, it was the object of the present invention to provide a glass-ceramic which has improved mechanical and optical properties and also improved chemical stability relative to the (glass-) ceramics known from the state of the art.

This object is achieved by the lithium disilicate glass-ceramic having the features of claim 1. In claim 2, uses according to the invention are indicated. Likewise, a shaped dental product having the features of claim 3 is provided.

Within the scope of the present invention, glass compositions have been developed which can be prepared in a two-step production process, are easy to machine after the first crystallisation step, in particular by means of CAD/CAM, and, after a very short second crystallisation step, are both highly-transparent and very strong and have better chemical stabilities than the known lithium disilicate glass-ceramics.

It was shown surprisingly that the addition of at least 10 wt. % $ZrO_2$ to certain glass compositions leads to glass-ceramics which can be machined very readily in an intermediate crystallisation step and, in the end state, have excellent strength values, exceptional translucence and significantly increased chemical stabilities.

It was shown that up to 20% by weight of a stabiliser selected from the group consisting of $ZrO_2$, $HfO_2$ or mixtures hereof can be incorporated in the glass without having a significant influence on the structure. Contrary to all expectations, the stabiliser does not hereby crystallise out as a separate crystal phase but remains in the remaining glass phase. As a result of the high proportion in the amorphous phase, the mechanical and chemical stabilities in this phase are hugely improved, which also leads to improved properties in the end product.

In particular the chemical stability can be improved via the composition of the remaining glass phase since the glass phase has a significantly higher solubility than the lithium disilicate and hence represents the weak point with respect to chemical attack. The extremely high solubility of the stabiliser ($ZrO_2$) in the glass phase is in particular remarkable since e.g. zirconium oxide acts in many silicate glass-ceramics as nucleation agent, i.e. crystallises out as first phase during a temperature treatment, and the actually sought crystal phase is facilitated and is deposited in a fine-crystalline manner on these $ZrO_2$ crystals.

As a result of the high proportions of stabiliser which remain essentially in the amorphous phase, the crystalline proportion is correspondingly restricted. As a result, and due to the low crystallite size of the lithium disilicate crystals, good translucence of the materials is produced after the second crystallisation. The translucence is however also further improved by the refractive index of the glass phase being increased in turn by the stabiliser and, consequently, being adapted to the refractive index of the lithium disilicate. In the case of glass-ceramics in which the refractive index of the amorphous matrix phase corresponds to the refractive index of the crystalline phase/phases, very good translucence properties are found, relatively irrespective of the crystallite size. In the glass-ceramics according to the invention, therefore all three points for the production of an extremely translucent glass-ceramic are fulfilled:

limited crystal phase proportion, small crystals (<500 nm), adapted refractive index of amorphous and crystalline phase.

The high proportion of stabiliser has the effect therefore in the glass-ceramic of improved chemical stability, higher strength values and improved translucence in several respects to corresponding glass-ceramics without or with only a low $ZrO_2$— or $HfO_2$ proportion.

The glass-ceramics according to the invention can be produced preferably by means of a method, in which a) an initial glass is produced which comprises the components of the glass-ceramic, b) the initial glass is subjected to a first heat treatment at a first temperature in order to produce a glass-ceramic which has lithium metasilicate as single or main crystal phase and c) this glass-ceramic is subjected to a second heat treatment in which the lithium metasilicate is converted with $SiO_2$ from the glass phase into lithium disilicate and subsequently lithium disilicate is present as single or main crystal phase.

The crystallisation to form lithium metasilicate preferably takes place at temperatures between 620° C. and 800° C., with times between 1 and 200 minutes, preferably between 650° C. and 750° C. for 10 to 60 minutes.

The crystallisation to form lithium disilicate preferably takes place at temperatures between 800° C. and 1,040° C., with times of 5 to 200 minutes, preferably between 800° C. and 870° C. for 5 to 30 minutes.

The subject according to the invention is intended to be explained in more detail with reference to the subsequent examples without wishing to restrict said subject to the special embodiments shown here.

EXAMPLES 1 TO 6

In examples 1 to 6, compositions of glasses with a high zirconium oxide content are indicated, which are converted by a two-step temperature treatment firstly into readily mechanically machinable lithium metasilicate glass-ceramics and subsequently into highly-translucent, very strong and chemically-stable lithium disilicate glass-ceramics.

The compositions with their components are represented in Table 1.

TABLE 1

|  | B1 | B2 | B3 | B4 | B5 | B6 |
| --- | --- | --- | --- | --- | --- | --- |
| $SiO_2$ | 66.9 | 65.8 | 65.5 | 63.7 | 63.5 | 63.5 |
| $Li_2O$ | 13.9 | 13.7 | 13.6 | 13.2 | 14.4 | 12.9 |
| $ZrO_2$ | 10.0 | 10.0 | 12.0 | 11.7 | 12.7 | 13.5 |
| $Al_2O_3$ | 3.2 | 3.1 | 3.1 | 3.0 | 3.3 | 3.5 |
| $P_2O_5$ | 3.0 | 3.0 | 3.0 | 2.9 | 3.1 | 3.4 |
| $K_2O$ | 2.9 | 2.9 | 2.9 | 2.8 | 3.0 | 3.2 |
| $CeO_2$ | — | 1.0 | — | 2.0 | — | — |
| $Er_2O_3$ | — | 0.2 | — | 0.3 | — | — |
| $Tb_2O_3$ | — | 0.3 | — | 0.3 | — | — |

The glasses were melted at 1,500° C. and poured into metal moulds to form blocks. The blocks were stress-relieved at 560° C. in the furnace and cooled slowly. For the different characterisation processes, the glass blocks were divided up and subjected to a first crystallisation treatment. For this purpose, the glasses were aged for 10 to 120 minutes at 600° C. to 750° C. As a result, glass-ceramics with strength values of 150 MPa to 220 MPa were produced. Exclusively lithium metasilicate was hereby established as crystal phase. In this state, machining by means of CAD/CAM methods is very readily possible.

With a second short crystallisation at 800° C. to 950° C. for 3 to 15 minutes, recrystallisation of the lithium metasilicate with amorphous $SiO_2$ from the glass phase takes place to form lithium disilicate and the result is an increase in strength to 300 MPa to 450 MPa. In addition to the lithium disilicate phase, a subsidiary crystal phase with a zirconium oxide content can hereby be produced. In addition, also small residues of lithium metasilicate can be present. The unequivocal main crystal phase is lithium disilicate.

In Table 2, the crystallisation conditions of individual glasses and also the resulting crystal phases and strength values are displayed.

TABLE 2

| Glass | B1 | B2 | B3 | B4 | B5 | B6 |
| --- | --- | --- | --- | --- | --- | --- |
| 1. Crystallisation | 650° C. 20 min | 700° C. 40 min | 650° C. 30 min | 700° C. 20 min | 700° C. 40 min | 700° C. 40 min |
| 2. Crystallisation | 850° C. 10 min | 830° C. 10 min | 870° C. 20 min | 850° C. 8 min | 820° C. 10 min | 830° C. 10 min |
| Crystal phases |  |  |  |  |  |  |
| Main phase (>80%) | disilicate | disilicate | disilicate | disilicate | disilicate | disilicate |
| Subsidiary phase (<20%) | — | — | — | — | metasilicate | metasilicate |
| Translucence | excellent | very good | excellent | very good | excellent | excellent |
| 3-point bending strength | 375 MPa | 413 MPa | 380 MPa | 418 MPa | 356 MPa | 385 MPa |

We claim:

1. A lithium silicate glass ceramic comprising at least 10 wt. % $ZrO_2$ and having a main crystal phase, wherein said main crystal phase is selected from the group consisting of lithium metasilicate crystal and lithium disilicate crystal.

2. The lithium silicate glass ceramic of claim 1, wherein the lithium silicate glass ceramic is present in the form of a dental restoration.

3. The lithium silicate glass ceramic of claim 1, wherein the lithium silicate glass ceramic is in the form of an inlay, an onlay, a bridge, a pin construction, a veneer, or a crown.

* * * * *